United States Patent [19]

Georgiev et al.

[11] Patent Number: 4,767,868

[45] Date of Patent: Aug. 30, 1988

[54] 3-PHENYL-3-(1H-IMIDAZOL-1-YLMETHYL)-2-METHYL-5-[(PHENYLAMINO)METHYL]ISOXAZOLIDINES

[75] Inventors: Vassil S. Georgiev, Rochester; George B. Mullen, Avon, both of N.Y.

[73] Assignee: Pennwalt Corporation, Philadelphia, Pa.

[21] Appl. No.: 36,830

[22] Filed: Apr. 10, 1987

[51] Int. Cl.[4] .................... A01N 43/52; C07D 233/60
[52] U.S. Cl. ..................................... 548/240; 548/341
[58] Field of Search ........................................ 548/240

[56] References Cited

U.S. PATENT DOCUMENTS

| 3,709,901 | 1/1973 | Draber et al. | 548/235 |
| 3,711,495 | 1/1973 | Kulsa et al. | 548/240 |
| 3,915,978 | 10/1975 | Kulsa et al. | 548/240 |
| 3,987,179 | 10/1975 | Nadelson | 514/378 |
| 4,010,176 | 3/1977 | Kulsa et al. | 548/242 |
| 4,510,154 | 4/1985 | Yoshida et al. | 514/365 |
| 4,719,306 | 1/1988 | Georgien | 548/240 |
| 4,723,021 | 2/1988 | Georgien | 548/240 |

FOREIGN PATENT DOCUMENTS

| 171137 | 2/1986 | European Pat. Off. | 548/215 |
| 54-76579 | 6/1979 | Japan . | |

OTHER PUBLICATIONS

Kelly, R. C. et al., Chem. Abstract 93:114498u (1980), Abstracting German Offen. 2,918,878 (Nov. 22, 1979).
Haken, P. T. et al., Chem. Abstract 93:132471j: (1980), Abstracting Brit. Pat. Appln. 2,024,218 (Jan. 9, 1980).
Takahi, Y. et al., Chem. Abstract 81:22233c (1974), Abstracting Japan Kokai 7399,336 (Dec. 15, 1973).
Boyce, C. B. et al., Chem. Abstract 87:23258a (1977), Abstracting German Offen. 2,639,189 (Mar. 10, 1977).
Funaki, Y. et al., Chem. Abstract 92:128915u (1980), Abstracting Japan Kokai 79, 76,579 (Jun. 19, 1979).
Sokolov, S. V. et al., Chemical Abstract 55:7399 (1961), Abstracting "Isoxazole Compounds III, Synthesis of Some Isoxazolylazoles", Zhur. Obshchei Khim. 30 pp. 1781–1787 (1960).
Kano, H. et al., Chem. Abstract 62:9139A (1965) Abstracting French 1,376,432 (Oct. 23, 1964).
Kano, H. et al., Chem. Abstract 63:8367a (1965), Abstracting French 1,380,177 (Nov. 27, 1964).

Primary Examiner—Donald G. Daus
Assistant Examiner—Mark W. Noel

[57] ABSTRACT

3-Phenyl-3-(1H-imidazol-1-ylmethyl)-2-methyl-5-[(phenylamino)methyl]isoxazolidine and related derivatives in which hydrogens of their phenyl rings may be replaced by one or more halogen, lower alkoxy, lower alkyl and nitro groups are useful as antifungal agents.

8 Claims, No Drawings

3-PHENYL-3-(1H-IMIDAZOL-1-YLMETHYL)-2-METHYL-5-[(PHENYLAMINO)METHYL]ISOXAZOLIDINES

BACKGROUND OF THE INVENTION

This invention relates generally to substituted 2-methylisoxazolidines and more specifically to 3-phenyl-3-(1H-imidazol-1-ylmethyl)-2-methyl-5-[(phenylamino)methyl]isoxazolidine derivatives which are useful as antifungal agents.

BRIEF SUMMARY OF THE INVENTION

In accordance with this invention there are provided compounds of the formula:

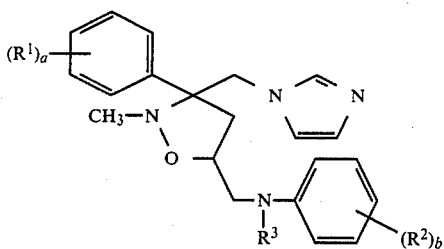

and the pharmaceutically acceptable acid addition salts thereof, in the form of their enantiomers or mixtures of their enantiomers including diastereoisomeric pairs of such enantiomers,
wherein,
a = 1 or 2,
b = 1 or 2,
$R^1$ is selected from hydrogen, lower alkyl, lower alkoxy, halogen, and combinations thereof, provided that the ortho position is hydrogen,
$R^2$ is selected from hydrogen, lower alkyl, lower alkoxy, halogen, nitro, and combinations thereof, and
$R^3$ is selected from hydrogen, lower alkyl and benzyl.

DETAILED DESCRIPTION OF THE INVENTION

The compounds of this invention are useful as antifungal agents. They have in vitro activity against yeast and systemic mycoses and dermatophytes as determined by broth and agar testing techniques [McGinnis, M. R., *Laboratory Handbook of Medical Mycology*, Academic Press, N.Y., N.Y. (1980)]. The compounds prepared in Examples 2-4 below were found to have good to moderate inhibitory activity against a broad spectrum of organisms including *Trichophyton mentagrophytes, Trichophyton rubrum, Trichophyton tonsurans, Trichophyton schoenleinii, Epidermophyton floccosum, Microsporum audouini, Microsporum canis, Candida albicans,* and *Candida stellatoidea* (minimum inhibitory concentration, MIC, of <0.2 to 70 ug/ml).

Because of the antifungal activity of the compounds of the invention they can be used, for example, in suitable liquid, semi-solid or solid carriers in the form of solutions, emulsions, suspensions, dispersions, ointments, aerosols, soaps, detergents, and powders in amounts effective to combat systemic and dermatophylic fungal infections in warm blooded animals (1 to 20 percent active ingredient).

The compounds of this invention are those of the formula:

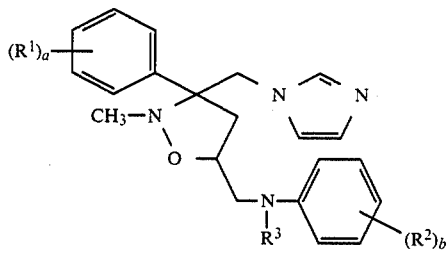

and the pharmaceutically acceptable acid addition salts thereof, in the form of their enantiomers or mixtures of their enantiomers including diastereoisomeric pairs of such enantiomers,
wherein,
a = 1 or 2,
b = 1 or 2,
$R^1$ is selected from hydrogen, lower alkyl, lower alkoxy, halogen, and combinations thereof, provided that the ortho position is hydrogen,
$R^2$ is selected from hydrogen, lower alkyl, lower alkoxy, halogen, nitro, and combinations thereof, and
$R^3$ is selected from hydrogen, lower alkyl and benzyl.

By halogen is meant chlorine, bromine, fluorine and iodine with chlorine and fluorine being preferred. By lower alkyl is meant such groups containing one to four (1-4) carbons and lower alkoxy is meant such groups containing one to six (1-6) carbons. In either case such groups with three or more carbons can have a branched or unbranched chain. Compounds having ortho substitution of the 3-phenyl group were not prepared probably due to steric hindrance.

The 3-phenyl-3-(1H-imidazol-1-yl-methyl)-2-methyl-5-[(phenylamino)methyl]isoxazolidines of the invention are obtained as mixtures of cis- and trans-diastereomers due to the presence in the isoxazolidine ring of two asymmetric carbon atoms. The diastereomeric mixture is conveniently separated by flash-chromatography on silica gel using halogenated hydrocarbons (preferably dichloromethane and chloroform), alkanols (preferably methanol and ethanol), ethyl acetate and such as eluents. The eluents may be utilized alone or in combinations such as the ones comprised of 95-99% by volume halogenated hydrocarbon and 1-5% by volume alkanol. The stereochemistry of the two asymmetric carbon atoms in the isoxazolidine ring may be determined by conventional methods that include x-ray crystallography, nuclear magnetic resonance spectroscopy, circular dichroism or optical rotatory dispersion. Both the cis and trans stereoisomers are resolvable into their optical enantiomers with (+) and (−) optical rotations by standard techniques such as fractional recrystallization of the diastereomeric salts with optically active organic acids such as (+) and (−) -tartaric acid, (+) and (−) -dibenzoyltartaric acid and the like.

As illustrated in the following diagram, the 3-phenyl-3-(1H-imidazol-1-ylmethyl)-2-methyl-5-[(phenylamino)methyl]isoxazolidines of the invention can be synthesized by an initial reaction of properly substituted phenyl (imidazol-1-ylmethyl) ketones with N-methylhydroxylamine to provide the corresponding nitrone compound 1. The preparation of such nitrones is described in our copending application Ser. No. 900,856 filed Aug. 27, 1986 whose disclosure is incorporated herein by reference. Compound 1 is then treated with an appropriate 3-(phenylamino)prop-1-ene (2) to give a cis-/trans-diastereomeric mixture of the desired 3-phenyl-3-(1H-imidazol-1-ylmethyl)-2-methyl-5-[(phenylamino)methyl]isoxazolidine derivative 3.

The synthesis of compounds 2 is accomplished by the procedures of Rodriguez and Canoira [J. Heterocyclic Chem., 22, 883–888 (1985)], and Laurent et al. [Synthesis (9), 685–700 (1983)].

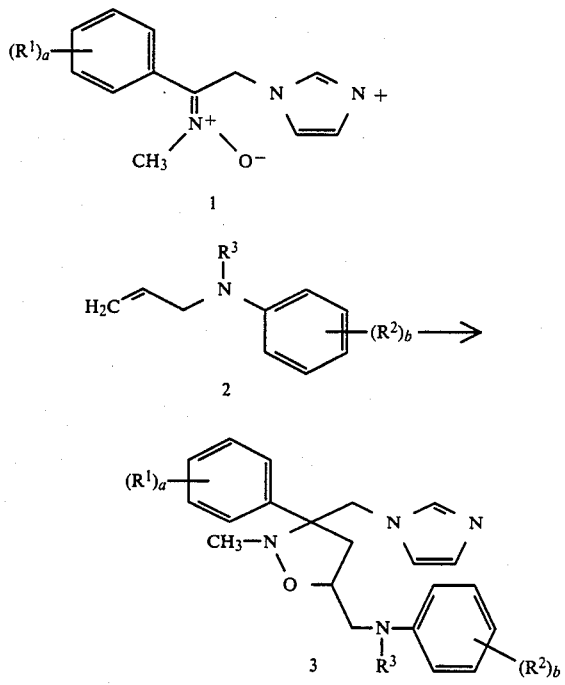

The compounds of the invention are all basic and thus can form salts with pharmaceutically acceptable inorganic and organic acids such as, for example, acetic acid, maleic acid, malic acid, fumaric acid, succininc acid, succinamic acid, tartaric acid, citric acid, lactic acid, hydrochloric acid, hydrobromic acid, hydroiodic acid, nitric acid, sulfuric acid and phosphoric acid.

EXAMPLE 1

3-Phenyl-3-(1H-imidazol-1-ylmethyl)-2-methyl-5-{[N-phenyl-N-(phenylmethyl)amino]methyl}isoxazolidine (3: $R^1=R^2=H$, $R^3=CH_2C_6H_5$)

A solution of 5.3 g (24.6 mmol) of 1-phenyl-2-(1H-imidazol-1-yl)-N-methylethanimine N-oxide (1: $R^1=H$) [prepared by reacting 2-(1H-imidazol-1-yl)acetophenone (5.88 g, 0.032 mol), N-methylhydroxylamine hydrochloride (3.17 g, 0.038 mol), and NaOAc (6.24 g, 0.076 mol) in 50 ml of ethanol] and 10.2 g (45.7 mmol) N-phenyl-N-(phenylmethyl)-2-propen-1-amine (2: $R^2=H$, $R^3=CH_2C_6H_5$) [prepared by reacting 11.88 g (64.8 mmol) of N-benzylaniline with 8.4 ml (11.76 g, 97.2 mmol) of allyl bromide and 5.84 g (55.1 mmol) of sodium carbonate in 75 ml of 80% aqueous ethanol] in 150 ml of toluene is refluxed under a nitrogen atmosphere for 27 hours. Upon cooling to room temperature, the solvent is removed under reduced pressure. The residual dark oil is flash-chromatographed on neutral silica gel, using a mixture of chloroform-methanol (98:2 by volume) as eluent, to give 5.72 g (53%) of isomer A (3: $R^1=R^2=H$, $R^3=CH_2C_6H_5$). Mp 171°–176° C. (ethyl acetate).

Anal. Calcd for $C_{28}H_{30}N_4O$: C, 76.68; H, 6.89; N, 12.77. Found: C, 76.03; H, 7.11; N, 12.76.

EXAMPLE 2

3-(4-Chlorophenyl)-3-(1H-imidazol-1-ylmethyl)-2-methyl-5-[(phenylamino)methyl]isoxazolidine (3: $R^1=4$-Cl, $R^2=R^3=H$)

Derivative 3 ($R^1=4$-Cl, $R^2=R^3=H$) is obtained by a procedure similar to that described in Example 1 by reacting 1-(4-chlorophenyl)-2-(1H-imidazol-1-yl)-N-methylethanimine N-oxide (1: $R^1=4$-Cl) with N-phenyl-2-propen-1-amine (2: $R^2=R^3=H$). The product cis-/trans-diastereometric mixture is flash-chromatographed on neutral silica gel using chloroform-methanol (97:3 by volume) as eluent. Isomer A has a melting point of 159°–160° C. (ethyl acetate). Anal. Calcd for $C_{21}H_{23}ClN_4O$: C, 65.87; H, 6.05; N, 14.63; Cl, 9.26. Found: C, 65.77; H, 6.20; N, 14.42; Cl, 9.48. Isomer B has a melting point of 172°–173° C. (ethyl acetate).

EXAMPLE 3

3-(4-Chlorophenyl)-3-(1H-imidazol-1-ylmethyl)-2-methyl-5-{[4-chlorophenyl)amino]methyl}isoxoazolidine (3: $R^1=R^2=4$-Cl, $R^3=H$)

Derivative 3 ($R^1=R^2=4$-Cl, $R^3=H$) is prepared by a procedure similar to that described in Example 1 by reacting 1-(4-chlorophenyl)-2-(1H-imidazol-1-yl)-N-methylethanimine N-oxide (1: $R^1=4$-Cl) with N-(4-chlorophenyl)-2-propen-1-amine (2: $R^2=4$-Cl, $R^3=H$). Compound 3 ($R^1=R^2=4$-Cl, $R^3=H$) is flash-chromatographed on neutral silica gel using ethyl acetate as eluent. Isomer A has a melting point of 149°–150.5° C. (ethyl acetate). Anal. Calcd for $C_{21}H_{22}Cl_2N_4O$: C, 60.44; H, 5.31; N, 13.42; Cl, 16.99. Found: C, 60.40; H, 5.35; N, 13.27; Cl, 16.68.

EXAMPLE 4

3-(4-Chlorophenyl)-3-(1H-imidazol-1-ylmethyl)-2-methyl-5-{[(4-methoxyphenyl)amino]methyl}isoxazolidine (3: $R^1=4$-Cl, $R^2=4$-OCH$_3$, $R^3=H$)

Compound 3 ($R^1=4$-Cl, $R^2=4$-OCH$_3$, $R^3=H$) is prepared by a procedure similar to that described in Example 1 by reacting 1-(4-chlorophenyl)-2-(1H-imidazol-1-yl)-N-methylethanimine N-oxide (1: $R^1=4$-Cl) with N-(4-methoxyphenyl)-2-propen-1-amine (2: $R^2=4$-OCH$_3$, $R^3=H$). Derivative 3 ($R^1=4$-Cl, $R^2=4$-OCH$_3$, $R^3=H$) is flash-chromatographed on neutral silica gel using chloroform-methanol (99:1 by volume) as eluent. Isomer A has a melting point of 129°–132° (ethyl acetate). Anal. Calcd for $C_{22}H_{25}ClN_4O_2$: C, 63.99; H, 6.10; N, 13.57; Cl, 8.59. Found: C, 64.06; H, 6.10; N, 13.56; Cl, 8.58.

EXAMPLE 5

3-(4-Methoxyphenyl)-3-(1H-imidazol-1-ylmethyl)-2-methyl-5-{[(2-methylphenyl)amino]methyl}isoxazolidine (3: $R^1=4$-OCH$_3$, $R^2=2$-CH$_3$, $R^3=H$)

Derivative 3 ($R^1=4$-OCH$_3$, $R^2=2$-CH$_3$, $R^3=H$) is prepared by a procedure similar to that described in Example 1 by reacting N-(4-methoxyphenyl)-2-(1H-imidazol-1-yl)-N-methylethanimine N-oxide (1: $R^1=4$-OCH$_3$) with N-(2-methylphenyl)-2-propen-1-amine (2: $R^2=2$-CH$_3$, $R^3=H$). Compound 3 ($R^1=4$-OCH$_3$), $R^2=2$-CH$_3$, $R^3=H$) is flash-chromatographed on neutral silica gel using chloroform-methanol (98:2 by volume) as eluent. Isomer A has a melting point of 110°–111° C. (ethyl acetate). Anal. Calcd for $C_{23}H_{28}N_4O_2$: C, 70.38; H, 7.19; N, 14.27. Found: C, 69.87; H, 7.11; N, 14.09.

EXAMPLE 6

3-(3,4-Dichlorophenyl)-3-(1H-imidazol-1-ylmethyl)-2-methyl-5-{[(4-nitrophenyl)amino]methyl}isoxazolidine (3: $R^1=3, 4\text{-}Cl_2, R_2=4\text{-}NO_2, R^3=H$)

Compound 3 ($R^1=3, 4\text{-}Cl_2, R^2=4\text{-}NO_2, R^3=H$) is prepared by a procedure similar to that described in Example 1 by reacting 1-(3,4-dichlorophenyl)-2-(1H-imidazol-1-yl)-N-methylethanimine N-oxide (1: $R^1=3, 4\text{-}Cl_2$) with N-(4-nitrophenyl)-2-propen-1-amine (2: $R^2=4\text{-}NO_2, R^3=H$). Derivative 3 ($R^1=3, 4\text{-}Cl_2, R^2=4\text{-}NO_2, R^3=H$) is flash-chromatographed on neutral silica gel using chloroform-methanol (97:3 by volume) as eluent. Isomer A has a melting point of 133°–134° C. (ethyl acetate). Isomer B has a melting point of 147°–148° C. (ethyl acetate).

EXAMPLE 7

3-(3-Methylphenyl)-3-(1H-imidazol-1-ylmethyl)-2-methyl-5-[(N-phenyl-N-methylamino)methyl]isoxazolidine (3: $R^1=3\text{-}CH_3, R^2=H, R^3=CH_3$)

Compound 3 ($R^1=3\text{-}CH_3, R^2=H, R^3=CH_3$) is obtained by a procedure similar to that described in Example 1 by reacting 1-(3-methylphenyl)-2-(1H-imidazol-1-yl)-N-methylethanimine N-oxide (1: $R^1=3\text{-}CH_3$) with N-phenyl-N-methyl-2-propen-1-amine (2: $R^2=H, R^3=CH_3$). Derivative 3 ($R^1=3\text{-}CH_3, R^2=H, R^3=CH_3$) is flash-chromatographed on neutral silica gel using 98:2 by volume mixture of ethyl acetate-methanol as eluent. Isomer A has a melting point of 130°–134° C. (ethyl acetate).

Other compounds of the invention where $R^1$ includes mono- or disubstitution with lower alkyl and/or lower alkoxy are prepared starting with nitrones 1 formed from imidazolylacetophenones such as:
2-(1H-imidazol-1yl)-4′-methylacetophenone, mp 133°–137° C.,
2-(1H-imidazol-1-yl)-4′-chloro-3′-methylacetophenone, mp 116°–118° C.,
2-(1H-imidazol-1-yl)-3′-methoxyacetophenone, mp 111°–113° C., and
2-(1H-imidazol-1-yl)-4′-fluoroacetophenone, mp 150°–155° C.

Salts of compounds of the invention can be prepared as known in the art, for example, by dissolving the compound in a 10:1 by volume mixture of ethanol and aqueous acid such as HCl or $HNO_3$, evaporating the solvent, and then recrystallizing the crude salt, for example, from methanol-ether, 1:3 by volume in the case of HCl salts, and ethanol in the case of $HNO_3$ salts.

We claim:
1. A compound of the formula:

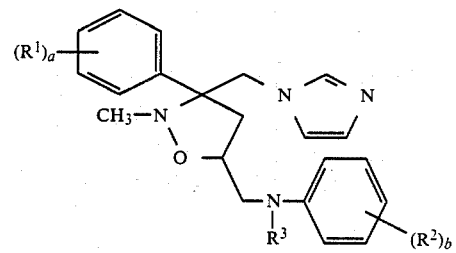

and the pharmaceutically acceptable acid addition salts thereof, in the form of their enantiomers or mixtures of their enantiomers including diastereoisomeric pairs of such enantiomers,
wherein,
a=1 or 2,
b=1 or 2,
$R^1$ is selected from hydrogen, lower alkyl, lower alkoxy, halogen, and combinations thereof, provided that the ortho position is hydrogen,
$R^2$ is selected from hydrogen, lower alkyl, lower alkoxy, halogen, nitro, and combinations thereof,
$R^3$ is selected from hydrogen, lower alkyl and benzyl.

2. The compound of claim 1 wherein the compound is 3-phenyl-3-(1H-imidazol-1-ylmethyl)-2-methyl-5-{[(N-phenyl-N-(phenylmethyl)amino]methyl}isoxazolidine.

3. The compound of claim 1 wherein the compound is 3-(4-chlorophenyl)-3-(1H-imidazol-1-ylmethyl)-2-methyl-5-[(phenylamino)methyl]isoxazolidine.

4. The compound of claim 1 wherein the compound is 3-(4-chlorophenyl)-3-(1H-imidazol-1-ylmethyl)-2-methyl-5-{[(4-chlorophenyl)amino]methyl}isoxazolidine.

5. The compound of claim 1 wherein the compound is 3-(4-chlorophenyl)-3-(1H-imidazol-1-ylmethyl)-2-methyl-5-{[(4-methoxyphenyl)amino]methyl}isoxazolidine.

6. The compound of claim 1 wherein the compound is 3-(4-methoxyphenyl)-3-(1H-imidazol-1-ylmethyl)-2-methyl-5-{[(2-methylphenyl)amino]methyl}isoxazolidine.

7. The compound of claim 1 wherein the compound is 3-(3,4-dichlorophenyl)-3-(1H-imidazol-1-ylmethyl)-2-methyl-5-{[(4-nitrophenyl)amino]methyl}isoxazolidine.

8. The compound of claim 1 wherein the compound is 3-(3-methylphenyl)-3-(1H-imidazol-1-ylmethyl)-2-methyl-5-[(N-phenyl-N-methylamino)methyl]isoxazolidine.

* * * * *